United States Patent
Dai et al.

(10) Patent No.: US 9,842,679 B2
(45) Date of Patent: Dec. 12, 2017

(54) POSS-CONTAINING IN-SITU COMPOSITE NANOGEL WITH MAGNETIC RESPONSIVENESS AND METHOD FOR PREPARING THE SAME

(71) Applicant: XIAMEN UNIVERSITY, Xiamen (CN)

(72) Inventors: Lizong Dai, Xiamen (CN); Lingnan Chen, Xiamen (CN); Yueguang Wu, Xiamen (CN); Birong Zeng, Xiamen (CN); Jie Mao, Xiamen (CN); Shuang Wang, Xiamen (CN); Yiting Xu, Xiamen (CN); Wei'ing Luo, Xiamen (CN); Kaibin He, Xiamen (CN); Xinyu Liu, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 0 days.

(21) Appl. No.: 15/038,734

(22) PCT Filed: Dec. 5, 2014

(86) PCT No.: PCT/CN2014/093076
§ 371 (c)(1),
(2) Date: May 23, 2016

(87) PCT Pub. No.: WO2015/096607
PCT Pub. Date: Jul. 2, 2015

(65) Prior Publication Data
US 2016/0379742 A1 Dec. 29, 2016

(30) Foreign Application Priority Data

Dec. 26, 2013 (CN) .......................... 2013 1 0731854

(51) Int. Cl.
| | |
|---|---|
| C08G 65/48 | (2006.01) |
| H01F 1/42 | (2006.01) |
| C08F 283/06 | (2006.01) |
| C08L 51/00 | (2006.01) |
| C07F 7/21 | (2006.01) |
| C08G 65/331 | (2006.01) |
| C08G 65/332 | (2006.01) |
| C08G 65/333 | (2006.01) |
| C08G 65/336 | (2006.01) |
| H01F 1/03 | (2006.01) |
| H01F 1/00 | (2006.01) |

(52) U.S. Cl.
CPC ................. *H01F 1/42* (2013.01); *C07F 7/21* (2013.01); *C08F 283/06* (2013.01); *C08G 65/331* (2013.01); *C08G 65/332* (2013.01); *C08G 65/336* (2013.01); *C08G 65/3326* (2013.01); *C08G 65/33317* (2013.01); *C08G 65/48* (2013.01); *C08L 51/00* (2013.01); *H01F 1/0063* (2013.01); *H01F 1/0315* (2013.01); *C08G 2220/00* (2013.01)

(58) Field of Classification Search
CPC .............................. C08K 5/549; H01F 1/344
See application file for complete search history.

(56) References Cited

FOREIGN PATENT DOCUMENTS

| | | |
|---|---|---|
| CN | 201110301103.8 | 5/2012 |
| CN | 20130408122.X | 12/2013 |

OTHER PUBLICATIONS

Chen (Reactive & Functional Polymers, 73 (2013) 1022-1029).*
A metal-sensitive organic-inorganic hybrid surfactant: POSS-capped dipicolinic acid-functionalized poly(ethylene glycol) amphiphile, by Chen Lingnan, Zeng Birong, Xie Jianjie, Yu Shirong, Yuan Conghui, Pan Yinyin, Luo Weiang, Liu Xinyu, He Kaibin, Xu Yiting, Dai Lizong, published on Reactive & Functional Polymers 73 (2013) 1022-1029 English material.
Preparation and Superparamagnetic Property of the Fe3O4/Polymer Composite Microsphere, by Zeng, Birong et al.

* cited by examiner

*Primary Examiner* — Kuo-Liang Peng
(74) *Attorney, Agent, or Firm* — Rabin & Berdo, P.C.

(57) ABSTRACT

The present invention provides a POSS-containing in-situ composite nanogel with magnetic responsiveness and the method for preparing the same, wherein POSS-containing macromolecule capable of polymerizing and metal-coordination complexing is synthesized to complex with iron salt, $Fe^{2+}/Fe^{3+}$ salts are in-situ deposited via chemical coprecipitation, and crosslinking agent and initiator are added to induce polymerization so that POSS-containing nanogel ranges with magnetic responsiveness is obtained. The present invention is of professional design, feasible technique and simple operation, and prepared nanogel magnetic particles are well dispersed with excellent magnetic responsiveness, which possesses a good application prospect in medical diagnosis, sensor, catalyst carrier and biomaterial.

8 Claims, 3 Drawing Sheets

POSS-CONTAINING IN-SITU COMPOSITE NANOGEL WITH MAGNETIC RESPONSIVENESS AND METHOD FOR PREPARING THE SAME

FIELD OF THE INVENTION

The present invention relates to nanogel with magnetic responsiveness and the method thereof, and especially to a POSS-containing in-situ composite nanogel with magnetic responsiveness and the method for preparing the same.

BACKGROUND OF THE INVENTION

Nanogel is a colloid system which is uniformly dispersed into water with a particle size of 1~1000 nm. The molecular chain structure of nanogel intermediates between branched polymer and network polymers, and the internal structure of which is cross-linking network. The cross-linking point among molecular chains of nanogel could be chemical point formed by chemical bond or physical point formed by interaction of hydrogen bond, static or hydrophobic interaction. Intelligent nanogel is a nanogel capable of responding on external stimuli, which is also known as stimuli-responsive nanogel. The external stimuli include change of temperature, dispersion medium pH and ionic strength, along with light, magnetic field and particular chemicals or biological substance.

Polyhedral oligomeric silsesquioxane (POSS for short) is a kind of caged-shaped organic-inorganic hybrid molecule being characterized by super-hydrophobicity, Macroligand efficiency and nano-size, which present particular thermal property, optical property, magnetic property and acoustic property. Therefore, POSS-based polymer is hailed as new generation of high-performance polymer.

In the last decade, intelligent nanogel shows attractive application prospect as Nanotechnology, biomedicine and intelligent material developed, and researches on its preparation, relationship between structure and property and application are getting more and more attention. Chinese patent No. CN102766267A discloses a method for preparing magnetic nanoparticle-containing chitosan hydrogel via adding magnetic nanoparticle dispersion into chitosan acetic acid solution and adding crosslinking agent for reacting to get the chitosan hydrogel. The entrapping method is simple; however, agglomeration and deposition of magnetic nanoparticle may occur during gel process, which may leads to misdistribution of magnetism. Chinese patent No. CN 102391603A discloses a method for preparing a novel magnetic polymer aquogel that iron ions are absorbed by sulfonate of aquogel under electrostatic interaction and then deposited via coprecipitation to generate $Fe_3O_4$ magnetic particles with a size of 50~100 nm. The method overcomes the problem of magnetic maldistribution, but the size of sol is too big to be applied in biomedicine. Chinese patent No. CN103242494A discloses a method for preparing composite microgel with sensibility of temperature, pH and magnetic, wherein superparamagnetic $Fe_3O_4$ particle is prepared with initiate center on its surface which is embedded by thermo-sensitive monomer and pH-sensitive monomer via Sedimentation and polymerization to obtain the composite microgel. However, the problem of magnetic misdistribution also remains. Chinese patent No. CN103304826A discloses a method for preparing magnetic chitosan hydrogel, wherein N-methyl acrylamide chitosan is capable of curing to hydrogel in UV light for 30 to 120 seconds and magnetism-induced patterned assembly of microgel is realizable, however, the processes are too complicated to practical application.

There is no report about POSS-containing in-situ composite nanogel with magnetic responsiveness at present.

SUMMARY OF THE INVENTION

The objective of present invention is to provide POSS-containing in-situ composite nanogel with magnetic responsiveness and the method for preparing the same.

The technical proposal of the present invention is that a POSS-containing in-situ composite nanogel with magnetic responsiveness is provided, the preparation of POSS-containing in-situ composite nanogel is that a kind of amphiphilic macromolecule (POSS-MA-PEG-DPA) which is polymerizable and capable of metal-coordination complexing adsorbs iron salts, the ferrous/ferric iron salts are in-situ precipitated via chemical coprecipitation to generate superparamagnetic $Fe_3O_4$ particles and then crosslinking agent is added for inducing polymerization to obtain stable nanogel; wherein the size of POSS-containing nanogel ranges from 100 to 300 nm, and the $Fe_3O_4$ particles with a size of 5~15 nm are uniformly dispersed on the polymer.

A method for preparing the POSS-containing in-situ composite nanogel with magnetic responsiveness comprises the steps of:

(1) dissolving POSS-MA-PEG-DPA in THF, adding the solution dropwise into deionized water under ultrasonic and rotary evaporating for removing THF to obtain POSS-MA-PEG-DPA aqueous solution A;

(2) adding iron salt solution containing $Fe^{2+}/Fe^{3+}$ dropwise into the solution A, stirring for 0.5 to 3 hours and then adding NaOH solution dropwise to obtain solution B;

(3) adding a crosslinking agent together with a initiator, heating up to 50~70° C. and reacting for 2 to 12 hours to obtain the POSS-containing in-situ composite nanogel with magnetic responsiveness.

The concentration of POSS-MA-PEG-DPA in the solution A ranges from 0.1 to 2 mg/mL.

In the iron salt solution, the concentration of ferrous iron salt ranges from 0.5 μmol/L to 10 μmol/L, and the concentration of ferric iron salt ranges from 1.0 μmol/L to 20 μmol/L.

The crosslinking agent is N,N'-Methylene-bis-acrylamide with a dosage of 0.1~1 wt % of POSS-MA-PEG-DPA; the initiator is ammonium persulphate or potassium persulphate with a dosage of 0.1~1.5 wt % of POSS-MA-PEG-DPA.

The structure formula of POSS-MA-PEG-DPA is as follows:

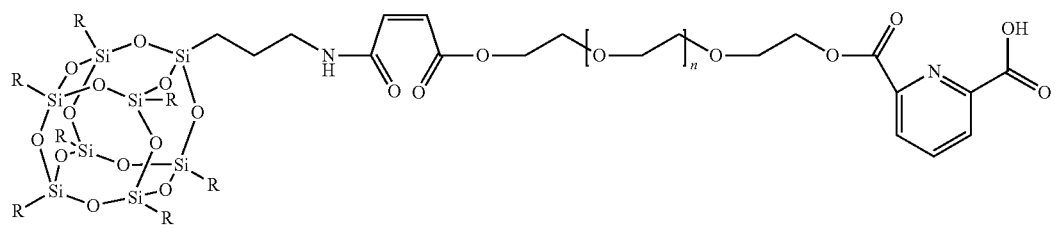

wherein R refers to organic corner group of POSS and n refers to degree of polymerization of polyethylene glycol (PEG);

wherein the function corner group of POSS is aminopropyl group and the rest seven corner groups are isobutyl groups.

The PEG has a molecular weight of 600~4000.

The preparation of POSS-MA-PEG-DPA comprises the steps of:

(1) dissolving aminopropyl POSS, maleic anhydride (MA) and a polymerization inhibitor into toluene, reacting at 90° C. for 24 hours and then separating and purifying to get POSS-MA;

(2) dissolving POSS-MA, PEG, the polymerization inhibitor and a catalyst into toluene, reacting at 135° C. for 36 hours and then separating and purifying to get POSS-MA-PEG;

(3) dissolving POSS-MA-PEG, 2,6-Pyridinedicarboxylic acid (DPA), the polymerization inhibitor and the catalyst into 1,4-dioxane, reacting at 125° C. for 24 hours and then separating and purifying to get POSS-MA-PEG-DPA.

The polymerization inhibitor is phenolic compound, quinines or aromatic nitro-compound.

The process of separating and purifying is evaporating solvent by rotary evaporator, extracting and depositing with mineral ether/aether solution (volume ratio of 1:1) and separating the deposition, then drying for 24 hours in vacuum oven.

The catalyst is toluene-p-sulfonic acid or concentrated sulfuric acid.

The dosage of polymerization inhibitor is 0.1~1 wt % of monomer.

The dosage of catalyst is 0.1~1 wt % of monomer.

The present invention employs POSS-containing amphiphilic macromolecule which is polymerizable and capable of metal-coordination complexing to complex with iron salt. $Fe^{2+}/Fe^{3+}$ salts are in-situ deposited via chemical coprecipitation, and crosslinking agent and initiator are added to induce polymerization so that POSS-containing nanogel ranges with magnetic responsiveness is obtained. The method of present invention is simple and controllable, which possesses a good application prospect in chemical-mechanical, biomedicine and tissue engineering as combination of stimuli-responsive and high mechanical property is realized.

DETAILED DESCRIPTION OF THE EMBODIMENTS

Figure 1:
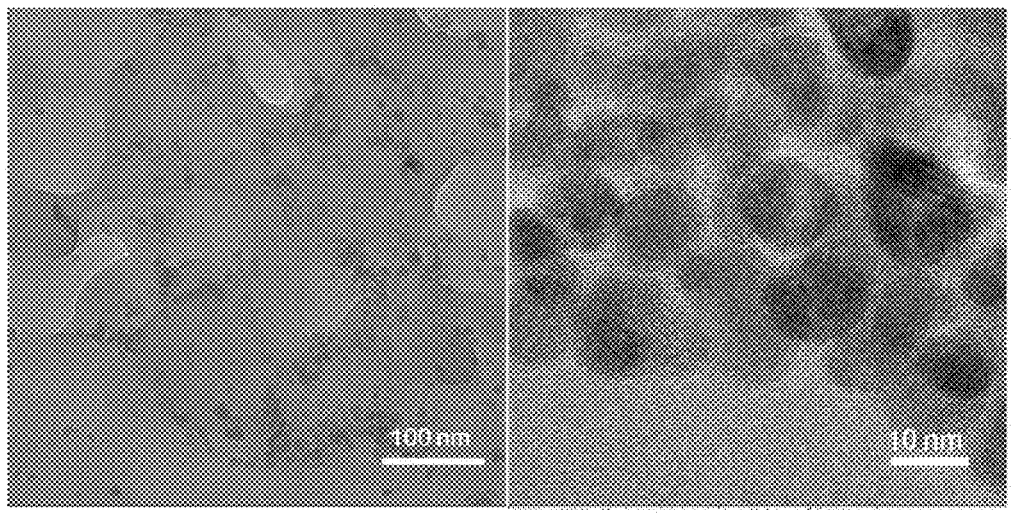
FIG. 1 illustrates TEM photo and high-resolution TEM photo of POSS-containing in-situ composite nanogel of the present invention.
Figure 2:
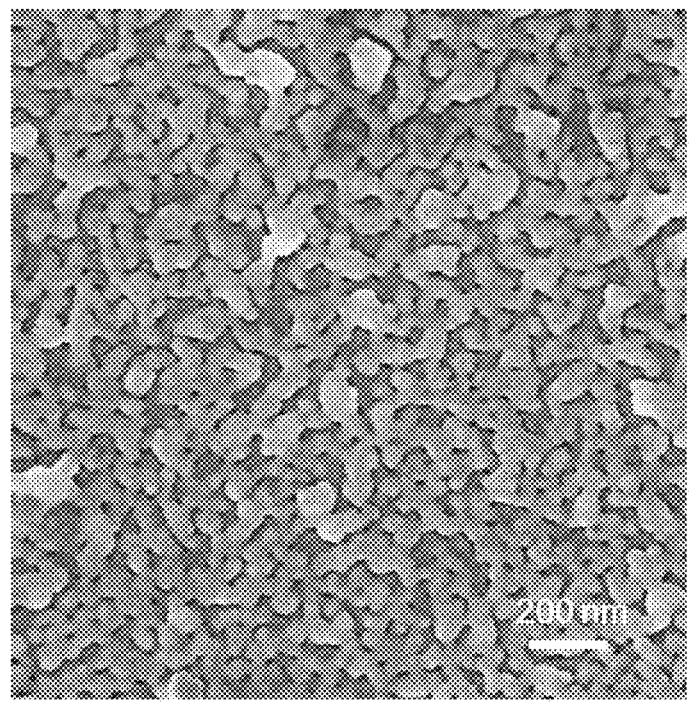
FIG. 2 illustrates SEM photo of POSS-containing in-situ composite nanogel of the present invention.
Figure 3:
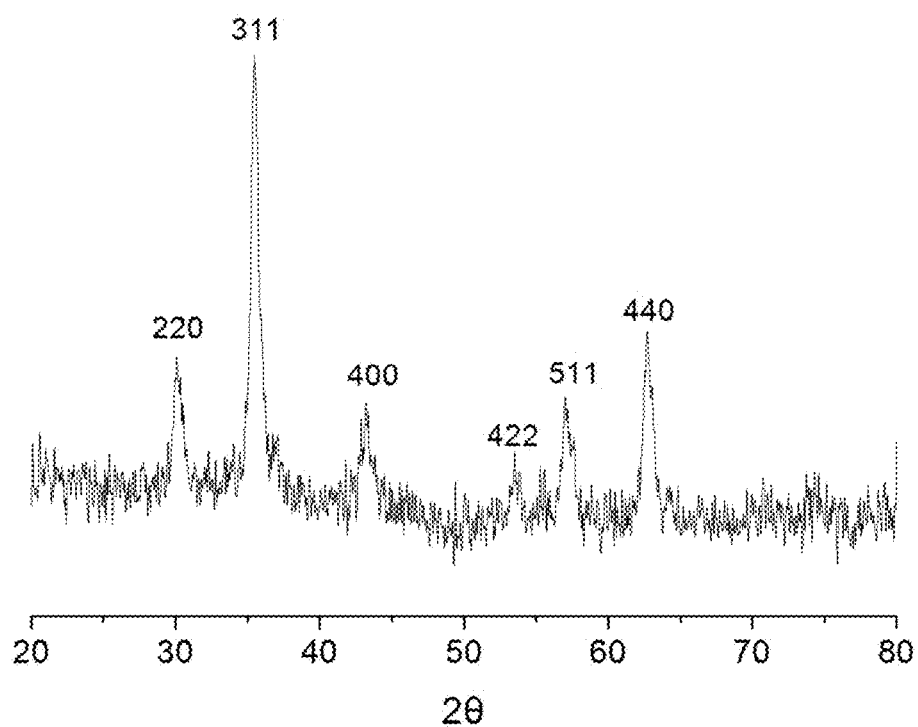
FIG. 3 illustrates XRD spectra of POSS-containing in-situ composite nanogel of the present invention.
Figure 4:
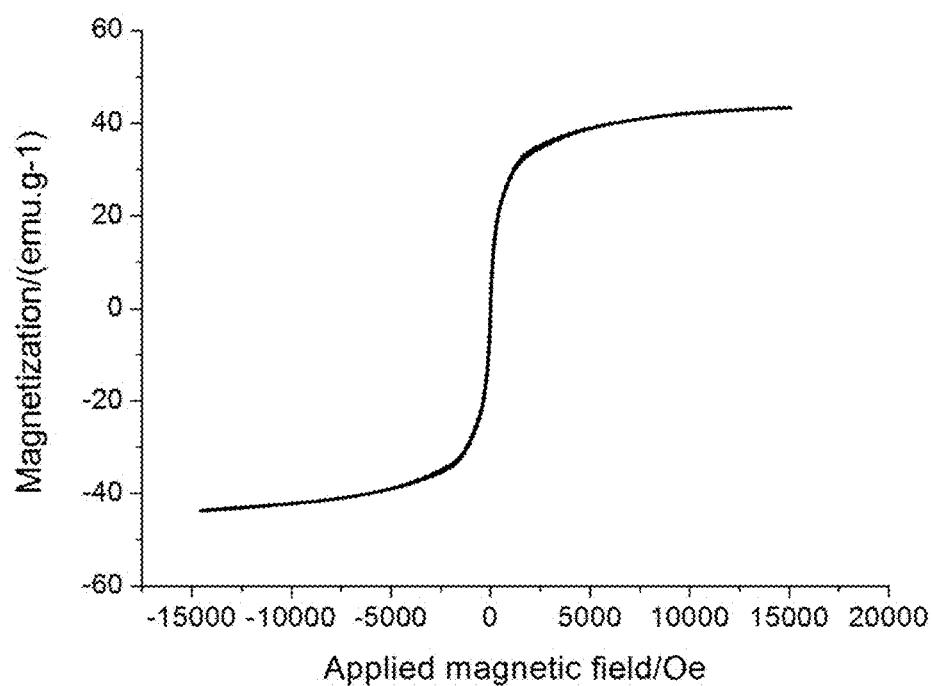
FIG. 4 illustrates hysteresis loop diagram of POSS-containing in-situ composite nanogel of the present invention.
Figure 5:
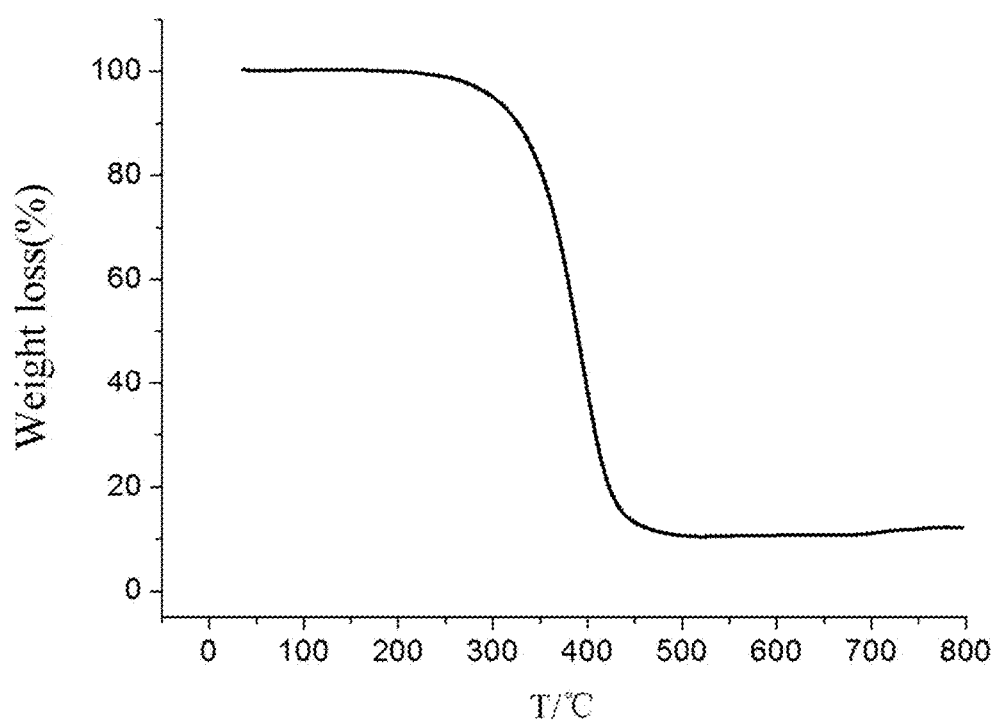
FIG. 5 illustrates thermal gravimetric diagram of POSS-containing in-situ composite nanogel of the present invention.

The present invention will be further described with the drawings and the embodiments.

Embodiment 1

(1) Preparation of POSS-MA-PEG-DPA Macromolecule 6 g POSS, 0.67 g maleic anhydride (MA), 0.034 g hydroquinone and 50 ml toluene are mixed together to react at 90° C. for 24 hours, and then the mixture is separated and purified to get POSS-MA; 1 g POSS-MA, 2.05 g PEG1000, 0.011 g p-toluenesulfonic acid, 0.0187 hydroquinone and 50 mL toluene are mixed together to react at 135° C. for 24 hours under nitrogen atmosphere, and then the mixture is separated and purified to get POSS-MA-PEG1000; 2 g POSS-MA-PEG1000, 0.078 g 2,6-Pyridinedicarboxylic acid (DPA), 0.0054 g p-toluenesulfonic acid, 0.0096 g hydroquinone and 50 mL 1,4-dioxane are mixed together to react at 125° C. for 24 hours, and then the mixture is separated and purified to get POSS-MA-PEG1000-DPA.

(2) Preparation of POSS-Containing In-Situ Composite Nanogel 0.50 g POSS-MA-PEG1000-DPA is dissolved in 10 mL THF to obtain solution A; 250 μL solution A is added dropwise into 10 mL deionized water under ultrasonic and the mixture is rotary evaporated for removing THF to obtain POSS-MA-PEG1000-DPA aqueous solution.

2.73 g $FeCl_3.6H_2O$ and 1.45 g $FeSO_4.7H_2O$ are dissolved in 100 mL deionized water to get $Fe^{2+}/Fe^{3+}$ salt solution; 100 μL $Fe^{2+}/Fe^{3+}$ salt solution is added dropwise into previous POSS-MA-PEG1000-DPA aqueous solution and stirred for 1 hours, then 100 μL NaOH of 0.44 mol/L is added and stirred for another 1 hours; 0.012 g N,N'-methylene-bis-acrylamide, 0.009 g ammonium persulphate are added and the mixture is heated up to 60° C. for 6 hours to obtain the POSS-containing in-situ composite nanogel.

The average particle size of the nanogel is 255.8 nm measured by DLS, and the saturation magnetic intensity of the nanogel is 32.9 emu/g measured by SQUID.

Embodiments 2 to 4

The methods for preparing POSS-containing in-situ composite nanogel of embodiments 2 to 4 are similar to embodiment 1 expect molecular weight of PEG is changed to 600, 2000 and 4000 respectively, and the results present on sheet 1.

Embodiments 5 to 8

The methods for preparing POSS-containing in-situ composite nanogel of embodiments 5 to 8 are similar to embodiment 1 expect dosage of $Fe^{2+}/Fe^{3+}$ salt solution is changed to 100 μL, 300 μL, 400 μL and 500 μL respectively, and the results present on sheet 2.

Sheet 1

| Embodiment | particle size of nanogel (nm) | saturation magnetic intensity of nanogel (emu/g) |
| --- | --- | --- |
| 2 | 235.4 | 31.6 |
| 3 | 267.8 | 33.8 |
| 4 | 296.9 | 31.2 |

Sheet 2

| Embodiment | particle size of nanogel (nm) | saturation magnetic intensity of nanogel (emu/g) |
| --- | --- | --- |
| 5 | 254.3 | 22.4 |
| 6 | 258.7 | 43.1 |
| 7 | 266.9 | 54.7 |
| 8 | 272..8 | 66.5 |

INDUSTRIAL APPLICABILITY

The present invention is of professional design, feasible technique and simple operation. Prepared nanogel magnetic particles are well dispersed with excellent magnetic responsiveness.

What is claimed is:

1. A POSS-containing in-situ composite nanogel with magnetic responsiveness, wherein the POSS-containing in-situ composite nanogel is derived from an amphiphilic macromolecule (POSS-MA-PEG-DPA), the amphiphilic macromolecule being polymerizable and capable of metal-coordination complex adsorption of iron salts; superparamagnetic $Fe_3O_4$ particles obtained by in-situ chemical coprecipitation of the ferrous/ferric iron salts; and a cross-linking agent added for inducing polymerization to obtain stable nanogel; wherein the size of POSS-containing nanogel ranges from 100 to 300 nm, and the $Fe_3O_4$ particles with a size of 5~15 nm are uniformly dispersed on the polymer.

2. A method for preparing the POSS-containing in-situ composite nanogel with magnetic responsiveness of claim 1 including the steps of:
dissolving POSS-MA-PEG-DPA in THF, adding the solution dropwise into deionized water under ultrasonic and rotary evaporating for removing THF to obtain POSS-MA-PEG-DPA aqueous solution A;
adding iron salt solution containing $Fe^{2+}/Fe^{3+}$ dropwise into the solution A, stirring for 0.5 to 3 hours and then adding NaOH solution dropwise to obtain solution B;
adding a crosslinking agent together with an initiator, heating up to 50~70° C. and reacting for 2 to 12 hours to obtain the POSS-containing in-situ composite nanogel with magnetic responsiveness.

3. The method according to claim 2, wherein the concentration of POSS-MA-PEG-DPA in the solution A ranges from 0.1 to 2 mg/mL.

4. The method according to claim 2, wherein in the iron salt solution, the concentration of ferrous iron salt ranges from 0.5 μmol/L to 10 μmol/L, and the concentration of ferric iron salt ranges from 1.0 μmol/L to 20 μmol/L.

5. The method according to claim 2, wherein the crosslinking agent is N,N'-Methylene-bis-acrylamide with a dosage of 0.1-1 wt % of POSS-MA-PEG-DPA; the initiator is ammonium persulphate or potassium persulphate with a dosage of 0.1~1.5 wt % of POSS-MA-PEG-DPA.

6. The method according to claim 2, wherein the structure formula of POSS-MA-PEG-DPA is as follows:

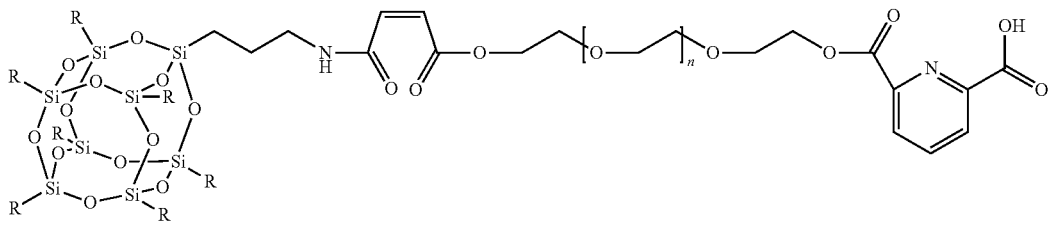

wherein R refers to organic corner group of POSS and n refers to degree of polymerization of polyethylene glycol (PEG), wherein the PEG has a molecular weight of 600~4000;

wherein the function corner group of POSS is aminopropyl group and the rest seven corner groups are isobutyl groups.

7. The method according to claim 2, wherein PEG has a molecular weight of 600-4000.

8. The method according to claim 2, wherein the method further includes steps of preparing the POSS-MA-PEG-DPA by:
dissolving aminopropyl POSS, maleic anhydride (MA) and a polymerization inhibitor into toluene, reacting at 90° C. for 24 hours and then separating and purifying to get POSS-MA;
dissolving POSS-MA, PEG, the polymerization inhibitor and a catalyst into toluene, reacting at 135° C. for 36 hours and then separating and purifying to get POSS-MA-PEG;
dissolving POSS-MA-PEG, 2,6-Pyridinedicarboxylic acid (DPA), the polymerization inhibitor and the catalyst into 1,4-dioxane, reacting at 125° C. for 24 hours and then separating and purifying to get POSS-MA-PEG-DPA.

* * * * *